United States Patent
Thornton

(10) Patent No.: US 6,305,376 B1
(45) Date of Patent: Oct. 23, 2001

(54) DEVICE AND METHOD FOR IMPROVING BREATHING

(76) Inventor: W. Keith Thornton, 5524 Edlen, Dallas, TX (US) 75220

( * ) Notice: Subject to any disclaimer, the term of this patent is extended or adjusted under 35 U.S.C. 154(b) by 0 days.

(21) Appl. No.: 09/554,771
(22) PCT Filed: Sep. 9, 1999
(86) PCT No.: PCT/US99/20495
§ 371 Date: May 16, 2000
§ 102(e) Date: May 16, 2000
(87) PCT Pub. No.: WO00/15283
PCT Pub. Date: Mar. 23, 2000

(51) Int. Cl.[7] .................................... A61F 5/56
(52) U.S. Cl. ............... 128/848; 128/859; 128/846; 602/902
(58) Field of Search ............... 128/846, 848, 128/859–862; 602/902

(56) References Cited

U.S. PATENT DOCUMENTS

| Re. 33,442 | 11/1990 | George ........................ 128/860 |
| 690,663 | 1/1902 | Pratt. |
| 746,869 | 12/1903 | Moulton. |
| 774,446 | 11/1904 | Moulton. |
| 885,196 | 4/1908 | Steil. |
| 893,213 | 7/1908 | Whiteway. |
| 1,076,534 | 10/1913 | Wallen. |
| 1,146,264 | 7/1915 | Kelly. |
| 1,483,694 | 2/1924 | Stukey. |
| 1,649,664 | 11/1927 | Carter. |
| 1,674,336 | 6/1928 | King. |
| 2,171,695 | 9/1939 | Harper ........................ 32/19 |
| 2,178,128 | 10/1939 | Waite ........................ 128/136 |
| 2,383,649 | 8/1945 | Heidbrink ........................ 128/142 |
| 2,424,533 | 7/1947 | Faires ........................ 128/136 |

(List continued on next page.)

FOREIGN PATENT DOCUMENTS

| 682724 | 2/1998 | (AU). |
| 692564 | 11/1998 | (AU). |
| 156627 | 12/1904 | (DE). |
| 2320501 | 11/1974 | (DE) ........................ A61F/5/56 |
| 3543931 | 6/1987 | (DE). |
| 3543931A1 | 6/1987 | (DE). |
| 3707952 | 9/1988 | (DE). |
| 3719009A1 | 12/1988 | (DE). |
| 29506512 | 6/1995 | (DE). |
| 19524534 | 6/1996 | (DE). |
| 0312368 | 4/1989 | (EP) ........................ A61F/5/56 |
| 0359135 | 3/1990 | (EP). |
| 1569129 | 6/1980 | (GB) ........................ A61F/5/56 |
| 20294 | 5/1998 | (WO). |

OTHER PUBLICATIONS

Professional Positioners brochure, "Dedicated to excellence," 4 pages, Unknown.

Great Lakes Orthodontics, Ltd., "Nocturnal Airway Patency Appliance™ (NAPA)," General Instructions, 2 pages, Undated.

Schmidt–Nowara, et al., "Oral Appliances for the Treatment of Snoring and Obstructive Sleep Apnea: A Review," *Sleep*, 18(6):501–510, 1995.

(List continued on next page.)

Primary Examiner—Michael A. Brown
(74) Attorney, Agent, or Firm—Baker Botts L.L.P.

(57) ABSTRACT

A device (10) for improving the breathing of a user includes an upper arch (12) adapted to receive at least some of the user's upper teeth, a lower arch (14) adapted to receive at least some of the user's lower teeth, and an engager (104) that engages the lower arch (14). An adjustor (100) adjusts the engager (104) forwardly relative to the upper arch (12). A slotted plate (114) couples the adjustor (100) to the upper arch (12) and adjustably positions the lower arch (14) vertically relative to the upper arch (12).

19 Claims, 2 Drawing Sheets

U.S. PATENT DOCUMENTS

| | | | |
|---|---|---|---|
| 2,521,039 | 9/1950 | Carpenter | 128/136 |
| 2,521,084 | 9/1950 | Oberto | 128/141 |
| 2,531,222 | 11/1950 | Kesling | 32/14 |
| 2,574,623 | 11/1951 | Clyde | 128/136 |
| 2,590,118 | 3/1952 | Oddo, Jr. | 128/136 |
| 2,627,268 | 2/1953 | Leppich | 128/136 |
| 2,833,278 | 5/1958 | Ross | 128/136 |
| 2,867,212 | 1/1959 | Nunn, Jr. | 128/136 |
| 2,882,893 | 4/1959 | Godfroy | 128/136 |
| 3,037,501 | 6/1962 | Miller | 128/141 |
| 3,107,668 | 10/1963 | Thompson | 128/136 |
| 3,124,129 | 3/1964 | Grossberg | 128/136 |
| 3,132,647 | 5/1964 | Corniello | 128/136 |
| 3,219,033 | 11/1965 | Wallshein | 128/136 |
| 3,277,892 | 10/1966 | Tepper | 128/172.1 |
| 3,312,216 | 4/1967 | Wallshein | 128/136 |
| 3,321,832 | 5/1967 | Weisberg | 32/32 |
| 3,434,470 | 3/1969 | Strickland | 128/136 |
| 3,457,916 | 7/1969 | Wolicki | 128/136 |
| 3,513,838 | 5/1970 | Foderick et al. | 128/136 |
| 3,522,805 | 8/1970 | Wallshein | 128/136 |
| 3,658,058 | 4/1972 | Neidhart et al. | 128/147 |
| 3,854,208 | 12/1974 | Arant | 32/19 |
| 3,864,832 | 2/1975 | Carlson | 128/136 |
| 3,871,370 | 3/1975 | McDonald | 128/136 |
| 3,884,226 | 5/1975 | Tepper | 128/136 |
| 4,016,650 | 4/1977 | Leusner et al. | 32/17 |
| 4,026,024 | 5/1977 | Tradowsky | 32/19 |
| 4,114,614 | 9/1978 | Kesling | 128/136 |
| 4,169,473 | 10/1979 | Samelson | 128/136 |
| 4,182,312 | 1/1980 | Mushabac | 433/68 |
| 4,227,877 | 10/1980 | Tureaud et al. | 433/37 |
| 4,289,127 | 9/1981 | Nelson | 128/207.14 |
| 4,304,227 | 12/1981 | Samelson | 128/136 |
| 4,376,628 | 3/1983 | Aardse | 433/80 |
| 4,382,783 | 5/1983 | Rosenberg | 433/19 |
| 4,433,956 | 2/1984 | Witzig | 433/7 |
| 4,439,147 | 3/1984 | Magill et al. | 433/3 |
| 4,439,149 | 3/1984 | Devincenzo | 433/6 |
| 4,470,413 | 9/1984 | Warncke | 128/201.18 |
| 4,495,945 | 1/1985 | Liegner | 128/200.26 |
| 4,505,672 | 3/1985 | Kurz | 433/6 |
| 4,553,549 | 11/1985 | Pope et al. | 128/421 |
| 4,568,280 | 2/1986 | Ahlin | 433/6 |
| 4,569,342 | 2/1986 | von Nostitz | 128/136 |
| 4,593,686 | 6/1986 | Lloyd et al. | 128/136 |
| 4,602,905 | 7/1986 | O'Keefe, III | 433/41 |
| 4,639,220 | 1/1987 | Nara et al. | 433/69 |
| 4,655,213 | 4/1987 | Rapoport et al. | 128/205.25 |
| 4,669,459 | 6/1987 | Spiewak et al. | 128/136 |
| 4,676,240 | 6/1987 | Gardy | 128/207.14 |
| 4,715,368 | 12/1987 | George | 128/136 |
| 4,773,853 | 9/1988 | Kussick | 433/6 |
| 4,799,500 | 1/1989 | Newbury | 128/859 |
| 4,862,903 | 9/1989 | Campbell | 128/861 |
| 4,901,737 * | 2/1990 | Toone | 128/848 |
| 4,906,234 | 3/1990 | Voychehovski | 604/79 |
| 4,919,128 | 4/1990 | Kopala et al. | 128/207.18 |
| 4,932,867 | 6/1990 | Ueno | 433/69 |
| 4,955,393 | 9/1990 | Adell | 128/859 |
| 5,003,994 | 4/1991 | Cook | 128/848 |
| 5,018,533 | 5/1991 | Hawkins | 128/848 |
| 5,028,232 | 7/1991 | Snow | 433/24 |
| 5,042,478 | 8/1991 | Kopala et al. | 128/207.18 |
| 5,042,506 | 8/1991 | Liberati | 128/848 |
| 5,046,512 | 9/1991 | Murchie | 128/848 |
| 5,052,409 | 10/1991 | Tepper | 128/859 |
| 5,056,534 | 10/1991 | Wright | 128/848 |
| 5,078,600 | 1/1992 | Austin | 433/73 |
| 5,092,346 * | 3/1992 | Hays | 128/859 |
| 5,103,838 | 4/1992 | Yousif | 128/859 |
| 5,117,816 | 6/1992 | Shapiro et al. | 128/200.24 |
| 5,154,184 | 10/1992 | Alvarez | 128/848 |
| 5,154,609 | 10/1992 | George | 433/68 |
| 5,183,057 | 2/1993 | Syrop et al. | 128/845 |
| 5,188,529 | 2/1993 | Lüth | 433/68 |
| 5,267,862 | 12/1993 | Parker | 433/215 |
| 5,277,202 | 1/1994 | Hays | 128/848 |
| 5,284,161 | 2/1994 | Karell | 128/848 |
| 5,313,960 | 5/1994 | Tomasi | 128/848 |
| 5,316,020 | 5/1994 | Truffer | 128/848 |
| 5,365,945 * | 11/1994 | Halstrom | 128/848 |
| 5,373,859 | 12/1994 | Forney | 128/846 |
| 5,409,017 * | 4/1995 | Lowe | 128/848 |
| 5,427,117 | 6/1995 | Thornton | 128/848 |
| 5,537,994 | 7/1996 | Thornton | 128/204.18 |
| 5,558,090 | 9/1996 | James | 128/207.18 |
| 5,566,683 | 10/1996 | Thornton | 128/848 |
| 5,678,567 | 10/1997 | Thornton et al. | 128/848 |
| 5,687,715 | 11/1997 | Landis et al. | 128/207.18 |
| 5,718,244 | 2/1998 | Thornton | 128/864 |
| 5,720,302 | 2/1998 | Belfer | 128/848 |
| 5,752,510 | 5/1998 | Goldstein | 128/207.18 |
| 5,755,219 | 5/1998 | Thornton | 128/201.18 |
| 5,807,100 | 9/1998 | Thornton | 433/48 |
| 5,829,441 | 11/1998 | Kidd et al. | 128/848 |
| 5,846,082 | 12/1998 | Thornton | 433/215 |
| 5,954,048 | 9/1999 | Thornton | 128/201.18 |
| 5,983,892 | 11/1999 | Thornton | 128/201.26 |
| 6,012,455 | 1/2000 | Goldstein | 128/207.18 |
| 6,109,265 | 8/2000 | Frantz et al. | 128/848 |

OTHER PUBLICATIONS

George, "Treatment of Snoring and Obstructive Sleep Apnea with a Dental Device," *General Dentistry*, 5 pages, Jul.–Aug. 1993.

W. Keith Thornton, "Device and Method for Improving Breathing," U.S. appln. Ser. No. 08/837418, pending, Apr. 16, 1997.

W. Keith Thornton, "Device for Improving Breathing," U.S. appln. Ser. No. 08/852,526, abandoned, Jan. 3, 1996.

Database WOI, Section PQ, Week 9039, Derwent Publications, Ltd., London, GB XP–002116355—Abstract "Surgical Mouth Air Duct.", Dec. 15, 1989.

CPAP/PRO®. . . Introducing a New Comfort Level for CPAP Users!! brochure (2 pages), No date.

W. Keith Thornton, "Device for Improving Breathing," U.S. appln. Ser. No. 08/594,904, pending, Jan. 31, 1996.

W. Keith Thornton, "Apparatus for Prevention of Snoring and Improved Breathing During Sleep," U.S. appln. Ser. No. 08/828,523, pending, Mar. 31, 1997.

W. Keith Thornton, "Apparatus for Prevention of Snoring and Improved Breathing During Sleep," U.S. appln. Ser. No. 08/363,639, abandoned, Dec. 24, 1994.

W. Keith Thornton, "Method and Apparatus for Adjusting a Dental Device," U.S. appln. Ser. No. 08/787,529, pending, Jan. 21, 1997.

W. Keith Thornton and Andrew O. Jamieson, "Method and Apparatus for Adjusting a Dental Device," U.S. appln. Ser. No. 08/435,277, abandoned, May 5, 1995.

W. Keith Thornton and Andrew O. Jamieson, "Method and Apparatus for Adjusting a Dental Device," U.S. appln. Ser. No. 08/218,719, abandoned Mar. 24, 1994.

W. Keith Thornton and Andrew O. Jamieson, "Apparatus for Adjusting a Dental Device," U.S. appln. Ser. No. 08/501,437, abandoned, Sep. 18, 1995.

W. Keith Thornton and Andrew O. Jamieson, "Method and Apparatus for Adjusting a Dental Device," U.S. appln. Ser. No. 08/435,277, abandoned, May 5, 1995.

W. Keith Thornton and Andrew O. Jamieson, "Method and Apparatus for Adjusting a Dental Device," U.S. appln. Ser. No. 08/218,719, abandoned, Mar. 24, 1994.

*Mayo Clinic Heath Letter*, vol. 13, No. 7, "Snoring,", Jul. 1995.

Photocopies of 2–piece dental device manufactured by Currie–Gibson Dental Laboratory, Inc. prior to Apr. 13, 1993.

Farrar & McCarty, "A Clinical Outline of Temporomandibular Joint Diagnosis and Treatment," Normandie Study Group for TMJ Dysfunction, 3 pages, 1993.

* cited by examiner

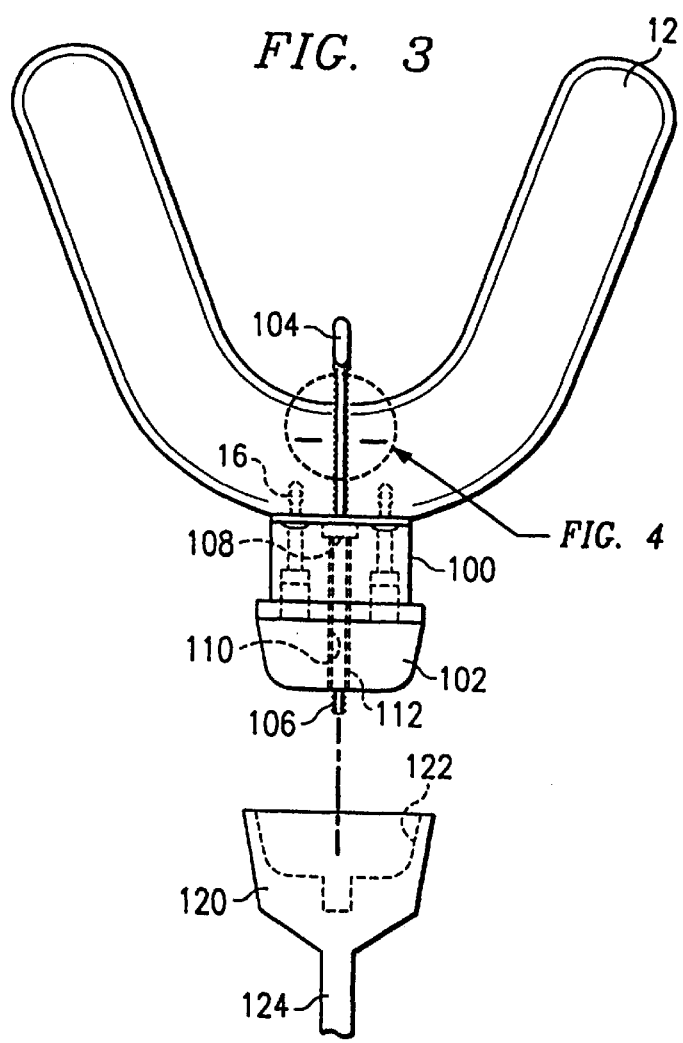
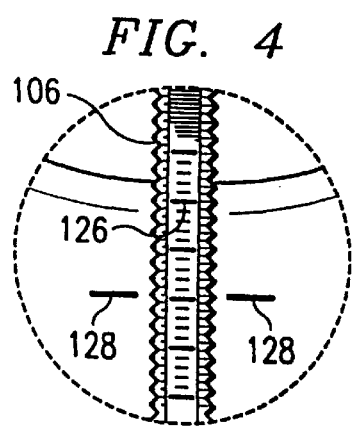
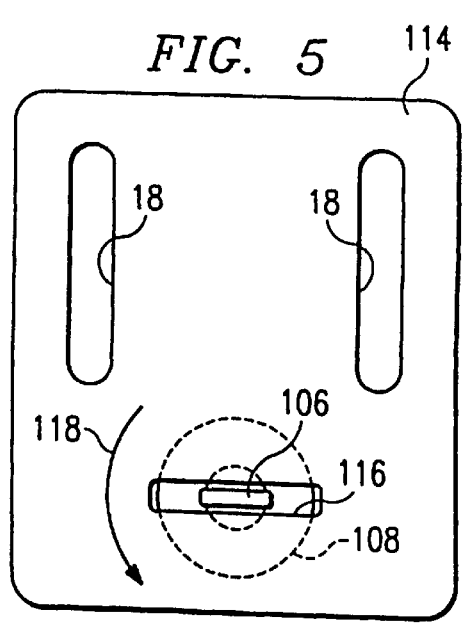

DEVICE AND METHOD FOR IMPROVING BREATHING

TECHNICAL FIELD OF THE INVENTION

This invention relates generally to medical and dental appliances, and more particularly to a device and method for improving breathing and method for fitting same.

BACKGROUND OF THE INVENTION

Many people experience breathing problems, which may result in difficulty sleeping, in snoring, or in other more serious conditions such as obstructive sleep apnea. One treatment for such breathing disorders involves the use of devices inserted into a user's mouth for extending the user's lower jaw forward, possibly in conjunction with a face mask for supplying air to the user. These devices open the breathing passageway more fully to allow easier breathing through the nose and mouth.

As technology continues to advance and users continue to demand increased comfort and performance, improving the breathing of users has become increasingly important. Previous devices for improving breathing have included upper and lower arches that are connected together outside a user's mouth and then inserted into the user's mouth as an integrated unit to position the user's lower jaw forward. Although these devices may treat some breathing problems, these devices do not sufficiently treat more serious conditions such as obstructive sleep apnea, while also allowing the user or a clinical professional to adjust the position of the user's lower jaw after the arches have been inserted into the user's mouth. Furthermore, these devices do not allow the forward and vertical positions of the lower jaw to be adjusted independently and relatively easily. Moreover, these devices are often unwieldy and uncomfortable for the user with respect to insertion into the user's mouth and subsequent use after insertion into the user's mouth. As a result of these and other deficiencies, such devices and methods for improving breathing are inadequate for the needs of many users.

SUMMARY OF THE INVENTION

In accordance with the present invention, disadvantages and problems associated with devices for improving breathing and methods for fitting such devices have been substantially reduced or eliminated.

According to one embodiment of the present invention, a device for improving the breathing of a user includes an upper arch adapted to receive at least some of the user's upper teeth, a lower arch adapted to receive at least some of the user's lower teeth, and an engager that engages the lower arch. An adjustor adjusts the engager forwardly relative to the upper arch. A slotted plate couples the adjustor to the upper arch and adjustably positions the lower arch vertically relative to the upper arch.

Important technical advantages of the present invention include providing a device for improving breathing that a user or clinical professional may adjust relatively easily to more optimally fit the user so as to provide increased comfort and performance. The present invention allows the position of the lower arch to be adjusted both forwardly and vertically relative to the upper arch, and allows the forward and vertical positions of the lower arch to be adjusted independently, according to particular needs. Furthermore, the present invention allows the forward and vertical positions of the lower arch to be adjusted while the device is inserted into the user's mouth. As a result, a user or clinical professional may adjust the relative positions of the lower arch and upper arch relatively easily to provide increased fit, comfort, and performance in treating breathing disorders such as obstructive sleep apnea. Other important technical advantages are apparent to one skilled in the art from the following figures, description, and claims.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which:

FIG. 3 illustrates an upper arch according to the present invention;

FIG. 4 illustrates indices and a zero set according to the present invention; and FIG. 5 illustrates a slotted plate having a slot for a hook according to the present invention.

DETAILED DESCRIPTION OF THE INVENTION

Figure 1:
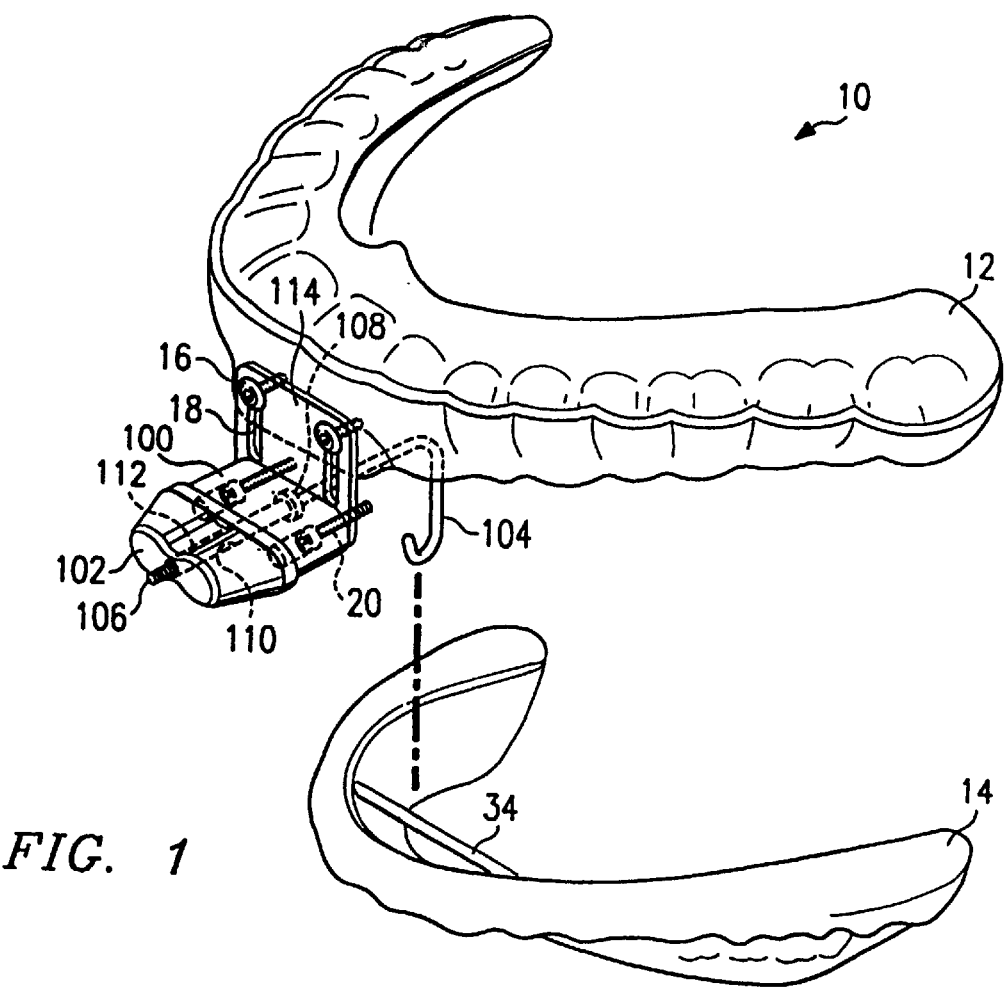
FIG. 1 illustrates a device for improving breathing according to the present invention.
Figure 2:
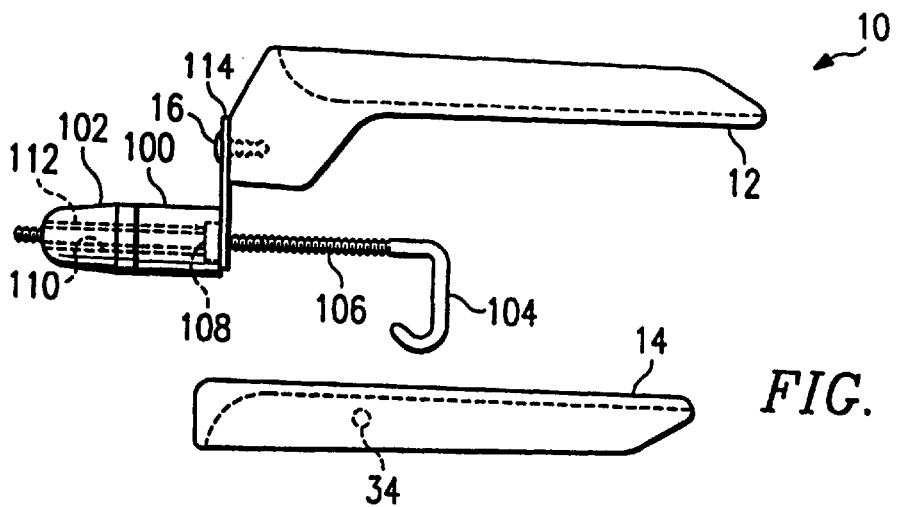
FIG. 2 illustrates a device for improving breathing according to the present invention.

FIGS. 1 and 2 illustrate a device 10 having an upper arch 12 adapted to receive one or more of a user's upper teeth. Device 10 also includes a lower arch 14 adapted to receive one or more of a user's lower teeth. Slotted plate 114 couples adjustor 100 to upper arch 12. Adjustor 100 may be coupled to slotted plate 14 using screws 20 or any other suitable technique. In one embodiment, slotted plate 114 is coupled to upper arch 12 using one or more screws 16 inserted through corresponding slots 18 in slotted plate 114 and into upper arch 12. Slotted plate 114 may be formed from stainless steel or any other suitable material. When screws 16 are sufficiently loosened, slotted plate 114 may be adjusted vertically to adjust the vertical position of adjustor 100 relative to upper arch 12. As discussed more fully below, adjustor 100 engages lower arch 14 such that forward or vertical adjustment of adjustor 100 results in forward or vertical adjustment, respectively, of lower arch 14 to improve the user's breathing.

Adjustor 100 includes a cylindrical or other suitable channel 110 that extends from the front of slotted plate 114 forward through adjustor 100 and into a rotating portion 102 of adjustor 100. A cylindrical coupler 112 includes a shaft disposed within channel 110 and an internally threaded head 108 that may rotate within adjustor 100 while engaged with threads on a shaft 106 of an engager 104. Although engager 104 is shown as being a hook, the present invention contemplates other suitable techniques for engaging lower arch 14, as discussed below. Cylindrical coupler 112 is fixedly coupled to rotating portion 102 of adjustor 100, such that when rotating portion 102 is rotated by hand or otherwise, cylindrical coupler 112 and head 108 of cylindrical coupler 112 are likewise rotated within channel 110. Although shaft 106 and cylindrical coupler 112 are shown as being accessible from the front of rotating portion 102 through a portion of channel 110, the present invention contemplates rotating portion 102 covering or otherwise completely isolating the forward portions of shaft 106 and cylindrical coupler 112, rotating portion 102 being integral to cylindrical coupler 112, or any other suitable configuration. Although rotating portion 102 and cylindrical coupler 112 may be formed from any suitable material, in one embodiment cylindrical coupler 112 is formed from stainless steel or another relatively inert metal, and rotating portion 102 is formed from a suitable thermoplastic material that forms upper arch 12.

In operation, arches 12 and 14 are inserted into the user's mouth, either separately or together, and engager 104 removably engages a clasp 34 of lower arch 14, which extends between opposite sides of lower arch 14. Clasp 34 may be any suitable rod or similar member that extends between opposite sides of lower arch. Clasp 34 may be substantially circular in cross section or may have any other suitable configuration. Although clasp 34 is shown as substantially linear, the present invention contemplates any clasp 34 suitable to be removably engaged by engager 104 so as to allow lower arch 14 to be adjusted forwardly and vertically relative to upper arch 12 in the manners discussed above. When engager 104 is engaged with clasp 34, lower arch 14 is allowed to move laterally relative to upper arch 12, providing increased comfort to the user and improved treatment of the user's breathing disorder.

When rotating portion 102 of adjustor 100 is rotated in an appropriate direction, internal threads of head 108 of cylindrical coupler 112, which are engaged with threads of shaft 106 of engager 104, rotate to adjust engager 104 forwardly relative to upper arch 12. This adjusts lower arch 14 forwardly relative to upper arch 12 and extends the user's lower jaw forwardly relative to upper arch 12 from its natural position to reduce or eliminate snoring, obstructive sleep apnea, or other breathing disorders. Although the present invention is described in terms of adjusting lower arch 14 and thus the user's lower jaw forwardly, device 10 also operates to adjust lower arch 14 and the user's jaw rearwardly relative to upper arch 12, according to particular needs.

As discussed above, slotted plate 114 may be adjusted vertically to adjust the vertical position of adjustor 100 and, by virtue of the engagement of lower arch 14, the vertical position of lower arch 14 relative to upper arch 12. Vertical adjustment of lower arch 14 may be upward or downward according to particular needs. In one embodiment, the forward and vertical adjustability of lower arch 14 allows the user's lower jaw to be extended forward to a fixed forward position and adjusted vertically to a fixed vertical position. As a result of the combined and independent adjustment of the forward and vertical positions of lower arch 14, the device of the present invention is able to provide increased fit, comfort, and performance.

FIG. 3 illustrates upper arch 12 of device 10. As shown in FIG. 3, in which upper arch 12 is shown from below, a connector 120 may be removably coupled to adjustor 100 of upper arch 12 to allow upper arch 12 to be removably coupled to a face mask. In one embodiment, at least a portion of adjustor 100, for example, some or all of rotating portion 102, is pressure fitted into a cavity 122 of connector 120. Shaft 124 of connector 120 may then be coupled to the face mask using an appropriate connecting apparatus.

In one embodiment, shaft 106 of engager 104 is substantially flattened, as discussed more fully below with reference to FIG. 5. In this case, only the rounded sides of shaft 106 are threaded and engage internal threads of head 108 of cylindrical coupler 112. As shown in exploded FIG. 4, engager 104 includes indices 126 that cooperate with zero set 128 to indicate the extent of forward or rearward adjustment of engager 104 relative to upper arch 12, which in turn indicates the extent of forward adjustment of lower arch 14 and therefore the user's lower jaw. Similar indices and zero set may be used in connection with slotted plate 114 to indicate the extent of vertical adjustment of lower arch 14 and therefore the user's lower jaw. Although indices 126 and zero set 128 are discussed, the present invention contemplates any suitable technique for indicating the extent to which the user's lower jaw is adjusted.

FIG. 5 illustrates slotted plate 114, shown from the rear, that adjustably couples adjustor 100 to upper arch 12. In addition to slots 18, slotted plate 114 includes a horizontal slot 116 through which shaft 106 of engager 104 extends through internally threaded head 108 of cylindrical coupler 112 and into the hollow interior of cylindrical coupler 112. In one embodiment, as discussed above, shaft 106 of engager 104 is substantially flattened, such that slot 116 limits or prevents rotation of shaft 106 when rotating portion 102 of adjustor 100 is rotated to rotate internally threaded head 108 of cylindrical coupler 112. As a result, engager 104 is adjusted forwardly relative to upper arch 12 in response to rotation of internally threaded head 108, for example, in the direction of arrow 118.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A device for improving the breathing of a user, comprising:
   an upper arch adapted to receive at least some of the user's upper teeth;
   a lower arch adapted to receive at least some of the user's lower teeth;
   an engager operable to engage the lower arch;
   an adjustor operable to adjust the engager forwardly; and
   a slotted plate coupling the adjustor to the upper arch and operable to adjust the position of the lower arch vertically from a first fixed position to a second fixed position while the upper and lower arches are inserted in the user's mouth to better fit the device to the user;
   the slotted plate defining at least one slot having a length in a substantially vertical direction and a width that is in a direction transverse to the length and is substantially smaller than the length.

2. The device of claim 1, wherein the slot is operable to receive a fastener.

3. The device of claim 1, wherein at least a portion of the adjustor is operable to be rotated to adjust the engager forwardly.

4. The device of claim 1, wherein the upper arch further comprises an engager slot through which at least a portion of the engager passes, the engager slot operable to limit the rotation of the engager.

5. The device of claim 1, wherein the adjustor comprises an internally threaded portion operable to engage threads of the engager.

6. The device of claim 1, wherein the lower arch comprises a clasp that extends laterally between opposite sides of the lower arch, the engager engaging the clasp to engage the lower arch.

7. The device of claim 1, wherein the device allows lateral movement of the lower arch.

8. A method for improving the breathing of a user, comprising:
- inserting an upper arch into the user's mouth, the upper arch adapted to receive at least some of the user's upper teeth;
- inserting a lower arch into the user's mouth, the lower arch adapted to receive at least some of the user's lower teeth;
- engaging the lower arch using an engager;
- adjusting the engager forwardly relative to the upper arch using an adjustor; and
- adjusting a slotted plate coupling the adjustor to the upper arch to adjust the position of the lower arch vertically from a first fixed position to a second fixed position while the upper and lower arches are inserted in the user's mouth to better fit the device to the user.

9. The method of claim 8, wherein adjusting the slotted plate comprises:
- sliding the slotted plate about a fastener passing through the slotted plate; and
- securing the fastener to fix the vertical position of the slotted plate.

10. The method of claim 8, wherein adjusting the engager forwardly comprises rotating at least a portion of the adjustor.

11. The method of claim 8, wherein the slotted plate comprises an engager slot through which at least a portion of the engager passes, the engager slot limiting the rotation of the engager.

12. The method of claim 8, further comprising engaging threads of the engager with an internally threaded portion of the adjustor.

13. The method of claim 8, wherein engaging the lower arch comprises engaging a clasp extending laterally between opposite sides of the lower arch.

14. The method of claim 8, further comprising allowing lateral movement of the lower arch after the device has been inserted into the user's mouth.

15. A method for fitting a device for improving the breathing of a user, comprising:
- inserting an upper arch into the user's mouth, the upper arch adapted to receive at least some of the user's upper teeth;
- inserting a lower arch into the user's mouth, the lower arch adapted to receive at least some of the user's lower teeth;
- engaging the lower arch using an engager after the upper arch and the lower arch have been inserted into the user's mouth;
- adjusting the engager forwardly relative to the upper arch using an adjustor after the upper arch and the lower arch have been inserted into the user's mouth; and
- adjusting a slotted plate coupling the adjustor to the upper arch after the upper arch and the lower arch have been inserted into the user's mouth to adjust the position of the lower arch vertically from a first fixed position to a second fixed position to better fit the device to the user.

16. The method of claim 15, wherein adjusting the slotted plate comprises:
- sliding the slotted plate about a fastener passing through the slotted plate; and
- securing the fastener to fix the vertical position of the slotted plate.

17. The method of claim 15, wherein adjusting the engager forwardly comprises rotating at least a portion of the adjustor.

18. The method of claim 15, wherein the slotted plate comprises an engager slot through which at least a portion of the engager passes, the engager slot limiting the rotation of the engager.

19. The method of claim 15, further comprising engaging threads of the engager with an internally threaded portion of the adjustor.

* * * * *